US012727776B2

(12) United States Patent
Wang et al.

(10) Patent No.: US 12,727,776 B2
(45) Date of Patent: Sep. 8, 2026

(54) SENSING MODULE AND WEARABLE DEVICE

(71) Applicant: NATIONAL TSING HUA UNIVERSITY, Hsinchu City (TW)

(72) Inventors: Ting-Wei Wang, Hsinchu City (TW); Chiu-Yun Huang, Hsinchu City (TW)

(73) Assignee: NATIONAL TSING HUA UNIVERSITY, Hsinchu City (TW)

( * ) Notice: Subject to any disclaimer, the term of this patent is extended or adjusted under 35 U.S.C. 154(b) by 0 days.

(21) Appl. No.: 18/595,549

(22) Filed: Mar. 5, 2024

(65) Prior Publication Data

US 2025/0107722 A1 Apr. 3, 2025

(30) Foreign Application Priority Data

Oct. 2, 2023 (TW) ................................ 112137654

(51) Int. Cl.

*A61B 5/05* (2021.01)
*A61B 5/00* (2006.01)
*G04G 21/02* (2010.01)

(52) U.S. Cl.

CPC ................ *A61B 5/05* (2013.01); *A61B 5/681* (2013.01); *G04G 21/025* (2013.01); *A61B 2560/0443* (2013.01); *A61B 2562/0223* (2013.01)

(58) Field of Classification Search

None

See application file for complete search history.

(56) References Cited

U.S. PATENT DOCUMENTS

| | | | | |
|---|---|---|---|---|
| 5,967,986 | A * | 10/1999 | Cimochowski | A61B 5/0031 600/504 |
| 7,925,606 | B1 * | 4/2011 | Katzer | G16H 40/67 705/2 |
| 9,031,653 | B2 | 5/2015 | Mashiach | |
| 10,240,994 | B1 * | 3/2019 | Xu | G01L 9/0072 |
| 10,381,881 | B2 | 8/2019 | Wittenberg et al. | |
| 2008/0024133 | A1 | 1/2008 | Vaughan et al. | |
| 2008/0197845 | A1 * | 8/2008 | Trequattrini | G01R 33/383 324/309 |
| 2009/0306524 | A1 | 12/2009 | Muhlsteff et al. | |
| 2016/0169838 | A1 | 6/2016 | Nagarkar et al. | |
| 2019/0074724 | A1 * | 3/2019 | Wittenberg | H02J 50/10 |
| 2019/0393730 | A1 | 12/2019 | Wittenberg et al. | |
| 2021/0361965 | A1 | 11/2021 | Yakobson et al. | |

(Continued)

FOREIGN PATENT DOCUMENTS

| | | | |
|---|---|---|---|
| CN | 101495034 | A | 7/2009 |
| CN | 104736053 | A | 6/2015 |

(Continued)

*Primary Examiner* — Yi-Shan Yang

(74) *Attorney, Agent, or Firm* — Birch, Stewart, Kolasch & Birch, LLP

(57) ABSTRACT

A sensing module includes a first coil, a control component coupled to the first coil, and a shielding component positioned at least on a first side of the first coil. The control component is configured to drive the first coil to transmit a first emitting electromagnetic signal, and to receive an induction signal generated from the first coil induced due to a first feedback electromagnetic signal. The shielding component shields at least a portion of the first emitting electromagnetic signal transmitting toward a first direction.

18 Claims, 9 Drawing Sheets

(56) References Cited

U.S. PATENT DOCUMENTS

| | | | | |
|---|---|---|---|---|
| 2021/0401305 | A1* | 12/2021 | Sweeney | A61B 5/6862 |
| 2022/0071502 | A1 | 3/2022 | Peeters et al. | |
| 2022/0108833 | A1* | 4/2022 | Hong | G04G 17/04 |
| 2023/0405352 | A1* | 12/2023 | Harrington, III | A61N 5/06 |

FOREIGN PATENT DOCUMENTS

| | | | | |
|---|---|---|---|---|
| CN | 105727444 | A | | 7/2016 |
| CN | 112914579 | A | | 6/2021 |
| CN | 113453616 | A | | 9/2021 |
| EP | 3 454 454 | A1 | | 3/2019 |
| TW | 200724094 | A | | 7/2007 |
| TW | M524172 | U | * | 6/2016 |

* cited by examiner

SENSING MODULE AND WEARABLE DEVICE

BACKGROUND OF THE INVENTION

1. Field of the Invention

The present invention relates to a sensing module and a compatible wearable device. In particular, the present invention relates to a sensing module for eddy current induction measurement and a wearable device including the same.

2. Description of the Prior Art

Wearable devices (for example, smart bracelets or smart watches) have become a popular product nowadays because they are easy to integrate with mobile devices such as smartphones. To broaden the applications of wearable devices, well-known manufacturers have incorporated various sensors and sensing mechanisms into wearable devices. Therefore, wearable devices these days are no longer accessories for mobile devices; they are also health monitoring devices that can detect various physiological data of users.

When integrating multiple sensors into wearable devices, it needs to consider various interactions that may lead to measurement inaccuracy. In addition, wearable devices are subjected to a large variation of wearers and frequent changes in their operating environment, so the sensor's capability to resist interference and its characteristic of low interactive interference are key considerations.

Taking blood pressure and heart rate measurement as an example, most wearable devices these days use photoplethysmography (PPG) as the measurement mechanism. Through the principles of light penetration and reflection, photoplethysmography can trace the change of reflected light flux caused by changes in blood flow due to vascular pulsation on the back of the hand. The pulse signal is extracted from the change of reflected light flux for cardiovascular health monitoring. However, the interference resistance of photoplethysmography is often insufficient for wearable devices. For example, the penetration depth of light is limited to the skin, so only physiological information about the pulsation of capillaries or superficial arteries can be extracted. Furthermore, the wearer's skin color, tattoos, or other disturbances on the skin (such as clothing, hair, etc.) will also cause different depths of light penetration into the skin. In addition, if the fixed construction of the wearable device (for example, the watch strap) is not fixed well, which causes the wearable device to dislocate, slide, or form a gap between the device and the skin, the measurement might fail. Overcoming the limitations of photoplethysmography may require the use of higher energy light sources, which would restrain the continuity and accuracy of long-term cardiovascular monitoring.

Moreover, since what between the light-transmitting unit and the skin must be transparent and no light obstruction, the traditional optical sensing mechanism has great limitations on the design of wearable devices. In addition to a compromising appearance, the restrictions on light transmission will also simultaneously increase the difficulties in satisfying the dustproof, scratchproof, and waterproof requirements. As a result, the product development process would cost more on research and verification.

Instead of photoplethysmography, if other measurement mechanisms (for example, electrical or magnetic) are used, it would easily affect the signal transmission of the wearable device body or affect other sensors. Therefore, sensing modules with both interference resistance and low interactive interference are a major focus of research and development in this field.

SUMMARY OF THE INVENTION

An objective of the present invention is to provide a sensing module that can be integrated with a wearable device. The sensing mechanism of the sensing module, as well as its accuracy, is less likely to be affected by the wearing method or the user's dermatological conditions.

An objective of the present invention is to provide a sensing module that can be integrated with a wearable device. The sensing module will not be easily affected by other operating modules in the wearable device or the body of the wearable device during sensing.

The present invention provides a sensing module including a first coil, a control component coupled to the first coil, and a shielding component positioned at least on a first side of the first coil. The control component is configured to drive the first coil to transmit a first emitting electromagnetic signal, and to receive a first induction signal generated from the first coil in response to a first feedback electromagnetic signal; the shielding component shields at least a portion of the first emitting electromagnetic signal transmitting toward a first direction.

The present invention provides a wearable device including a wearing structure, a body combined with the wearable structure, and a sensing module. The body is positioned on the first side of the sensing module, and the shielding component of the sensing module is positioned at least between the body and the first coil of the sensing module.

The aforementioned sensing module can perform eddy current induction measurement on the conductive part (for example, blood, tissue fluid, or skin) within the wearing area through the coil. Eddy current induction measurement is a contactless measurement approach, and the penetration depth can be adjusted through the emission frequency and other parameters. It is not easily affected by skin or other non-conductive media in the transmission path, which leads to a better interference resistance. The sensing module also controls the range of the emitting electromagnetic signal transmitted by the coil through the shielding component. This makes the emitting electromagnetic signal more directional, which reduces the impact of the sensing module on other surrounding circuit components or sensing modules.

BRIEF DESCRIPTION OF THE APPENDED DRAWINGS

The drawings presented in this disclosure are intended to describe various embodiments of the invention. However, to simplify the drawings and/or highlight the content to be presented in the drawings, conventional structures and/or elements in the drawings may be drawn in a simple schematic manner or may be omitted. On the other hand, the number of elements in the drawings may be singular or plural. The drawings presented in this disclosure are to illustrate the embodiments only and are not limiting thereof.

DETAILED DESCRIPTION OF THE INVENTION

Any reference herein to elements using designations such as "first," "second," etc. generally does not limit the number or order of these elements. Rather, these names are used herein as a convenient way to distinguish between two or more elements or instances of elements. Therefore, it should be regarded as that the names "first," "second," etc. in the claims do not necessarily correspond to the same names in the written description. Furthermore, it should be regarded as that reference to the first and second elements does not imply that only two elements may be employed or that the first element must precede the second element. The words "comprises", "includes", "has", "contains", etc. used in this article are all open terms, which mean including but not limited to.

The term "coupled" is used herein to refer to a direct or indirect electrical coupling between two structures. For example, in an illustration of indirect electrical coupling, one structure may be coupled to another structure via passive components such as resistors, capacitors, or inductors.

In the present invention, the words "exemplary" and "for example" are used to mean "serving as an example, instance, or illustration". Any implementation or aspect described herein as "exemplary," "for example," is not necessarily to be construed as "preferred or advantageous over other aspects of the invention." The terms "approximately" and "approximately" as used herein with respect to a specified value or characteristic are intended to mean within a certain numerical value (e.g., 10%) of the specified value or characteristic.

Figure 1:
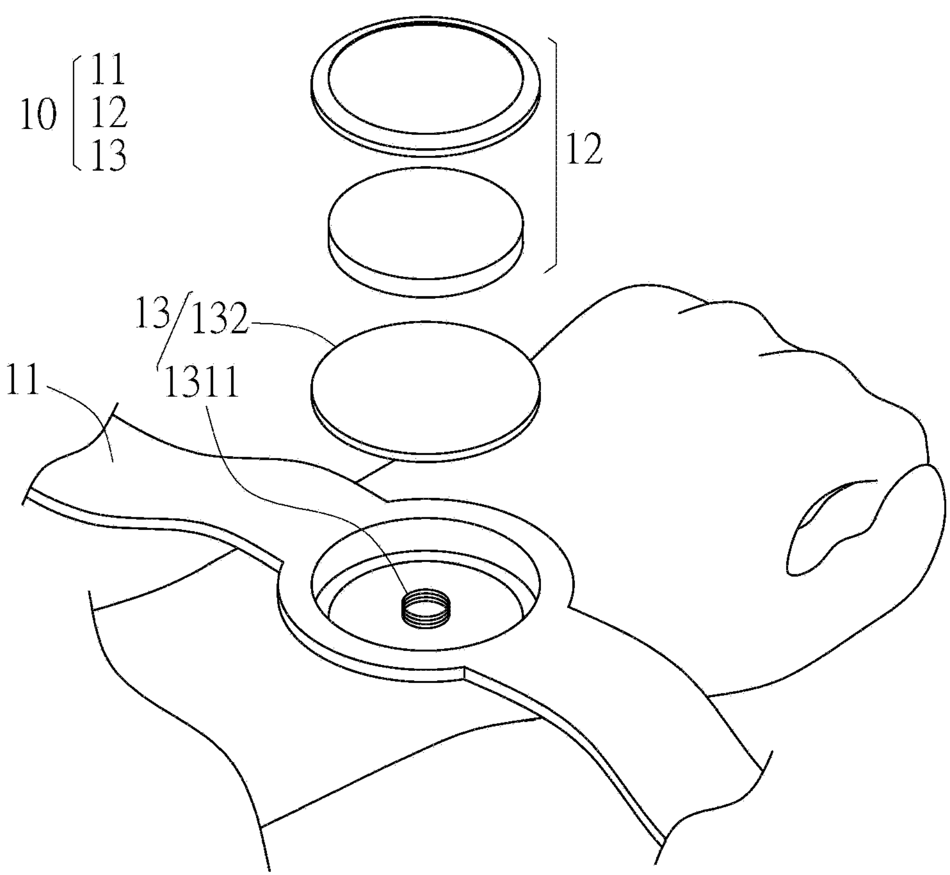
FIG. 1 is a schematic diagram of a wearable device in an embodiment of the present invention.

Please refer to FIG. 1, which illustrates a wearable device 10 including a wearable structure 11, a body 12 combined with the wearable structure 11, and a sensing module 13. The body 12 is positioned on the first side of the sensing module 13, and the shielding component 132 of the sensing module 13 is at least positioned between the body 12 and the first coil 1311 of the sensing module 13.

Specifically, the wearable device 10 is, for example, a watch, a smart bracelet, a smart watch, or a smart accessory, which is worn on the user's limbs or neck. The wearable structure 11 is, for example, a structure that fixes the wearable device 10 in a wearing position. Taking the wrist-worn device shown in FIG. 1 as an example, the wearing structure 11 is, for example, a watch strap. However, the wearing structure 11 is not limited to the example shown in FIG. 1. The body 12 of the wearable device 10 is defined, for example, as the part that implements specific functions of the wearable device. For example, for a watch, the main body 12 may be a dial, its clock hands, or a movement for rotating the clock hands. However, the main body 12 is not limited to the embodiment in FIG. 1. Taking a smart watch as an example, the main body 12 may be a display or a motherboard, etc. After the main body 12 is combined with the wearing structure 11, it can be placed at the part where the user wants to wear it through the wearing structure 11. The main body 12 is positioned on the first side S1 of the sensing module 13. Specifically, the sensing module 13 can be positioned at a location closer to the user's skin than the main body 12. In other words, the first side S1 of the sensing module 13 is the side relatively far away from the user's skin. The second side S2 of the sensing module 13, as opposed to the first side S1, is the side close to the user's skin. The shielding component 132 of the sensing module 13 is positioned between the body 12 and the coil (e.g. 1311) of the sensing module 13, to reduce the electromagnetic signal emitted toward the first side S1 after the coil is excited, and also to reduce the coil's exposure to noise from the first side S1 (e.g., from the main body 12). Accordingly, it reduces mutual interference between the sensing module 13 and the main body 12 after the sensing module 13 is installed on the wearable device 10.

Figure 2A:
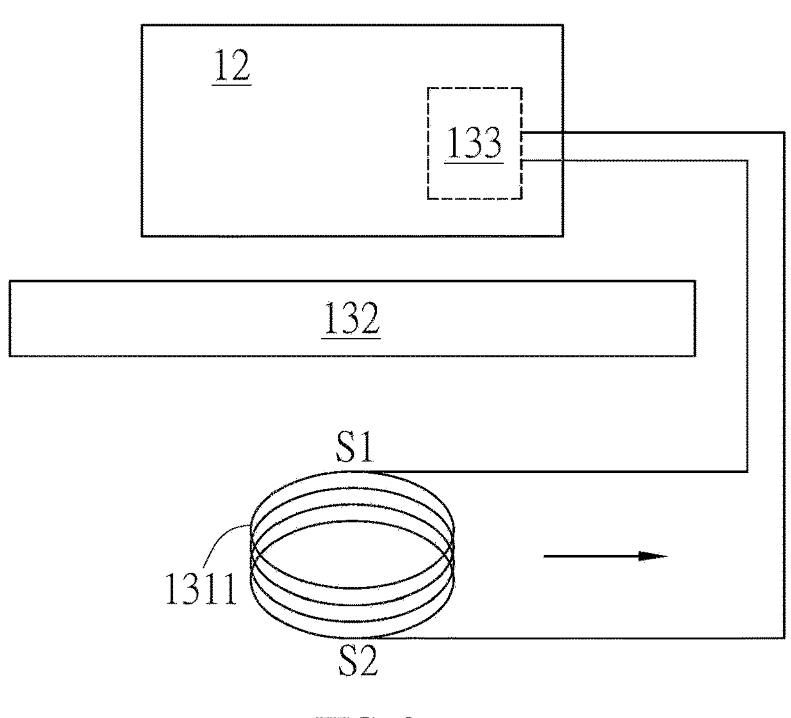
FIGS. 2A and 2B are schematic diagrams of the arrangement of the shielding component and the control component in an embodiment of the present invention.
Figure 2B:
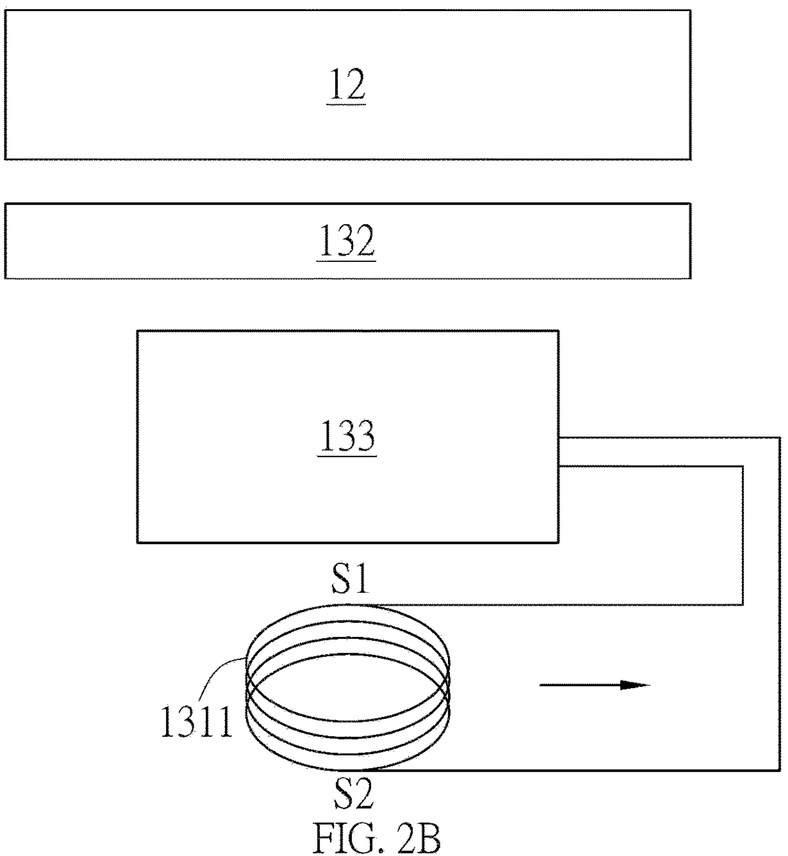

Please refer to the following paragraphs for various embodiments of the sensing module 13 of the present invention. First, please refer to FIG. 2A, FIG. 2B and FIG. 3. FIG. 2A and FIG. 2B respectively illustrate that the sensing module 13 of the present invention includes a first coil 1311, a control component 133 coupled to the first coil 1311, and at least a shielding component 132 positioned on the first side S1 of the coil 1311. The control component 133 is configured to drive the first coil 1311 to transmit the first emitting electromagnetic signal TS1, and receive the first induction signal SS1 generated from the first coil 1311 in response to the first feedback electromagnetic signal FS1. The shielding component 132 at least shields the portion of the first emitting electromagnetic signal TS1 toward a first direction (for example, the direction pointing from the first side S1 to the shielding component 132).

Specifically, the first coil 1311 of the present invention can be in a spiral shape, a ring shape, or other configurations with radiation-transmitting capabilities. In another aspect, the first coil 1311 may form a radiation-transmitting configuration through conductor lines on a hard or flexible substrate using conventional manufacturing techniques such as, but not limited to, etching, engraving, lithography, etc. However, the first coil 1311 of the present invention is not limited to the above examples, and any coil commonly known in the art should fall into the scope of the coil of the present invention.

The control component 133 can be coupled to the first coil 1311 through any conventional approach of electrical connection. For example, the control component 133 can be positioned on an arbitrary substrate (e.g., an FR4 or silicon substrate) and connected to the first coil 1311 through conductive lines. In another aspect, the control component 133 and the first coil 1311 can be positioned on the same substrate. For example, the first coil 1311 and the control component 133 may be positioned on the same substrate and connected via conductor lines on the substrate. However, the present invention is not limited to the aforementioned coupling method between the first coil 1311 and the control component 133.

Shielding component 132 may be any magnetic shielding component. For example, the magnetic shielding capability can be distinguished by material characteristics, such as a ferrite sheet. In another embodiment, the shielding component 132 can be a shielding circuit consisting of active/passive circuit components. The shielding component 132 can eliminate the electromagnetic signal emitted by the first coil 1311 from the first side S1 through mechanisms such as blocking, absorption, conversion, or cancellation. Exemplary arrangements of the shielding component 132, the control component 133, and the first coil 1311 are shown in FIGS. 2A and 2B. As shown in FIG. 2A, the shielding component 132 may be positioned between the control component 133 and the first coil 1311. For example, the control component 133 of the sensing module 13 of the present invention can be integrated with the body 12 of the wearable device 10. More specifically, the control component 133 of the sensing module 13 may be positioned on the circuit substrate of the body 12 of the wearable device 10 and be electrically coupled to the first coil 1311 through, for example, a conductor line. In this way, the shielding component 132 can shield the portion of the first emitting electromagnetic signal TS1 emitted by the first coil 1311 and directed toward the control component 133, so that the interference of the first emitting electromagnetic signal TS1 to the control component 133 is reduced. However, the control component 133 of the present invention is not limited to being integrated with the body 12. Alternatively, the control component 133 can be an independent element positioned on the first side S1 of the first coil 1311, and the control component 133 can be located outside of the shielding component 132 (i.e., the control component 133 can be located on the side of the shielding component 132 opposite to the first side S1).

In another aspect, as shown in FIG. 2B, the shielding component 132 can be positioned between the main body 12 of the wearable device 10 and the control component 133 (and the first coil 1311). In this way, the main body 12 of the wearable device 10 will be less susceptible to signal interference from the control component 133 and the first coil 1311. For example, when the body 12 of the wearable device 10 itself is a complete product, the development process of integrating the body 12, the control component 133, and the first coil 1311 of the wearable device 10 can be simplified by configuring the shielding component 132. It should be noted that the arranged position and the number of the shielding component 132 in FIG. 2A and FIG. 2B are only for illustration and are not intended to limit the present invention. The number of shielding components 132 of the present invention can be set according to the available space and interference resistance requirements of the wearable device 10.

Figure 3:
FIG. 3 is a schematic diagram of the sensing module performing eddy current induction measurement in an embodiment of the present invention.
Figure 3:
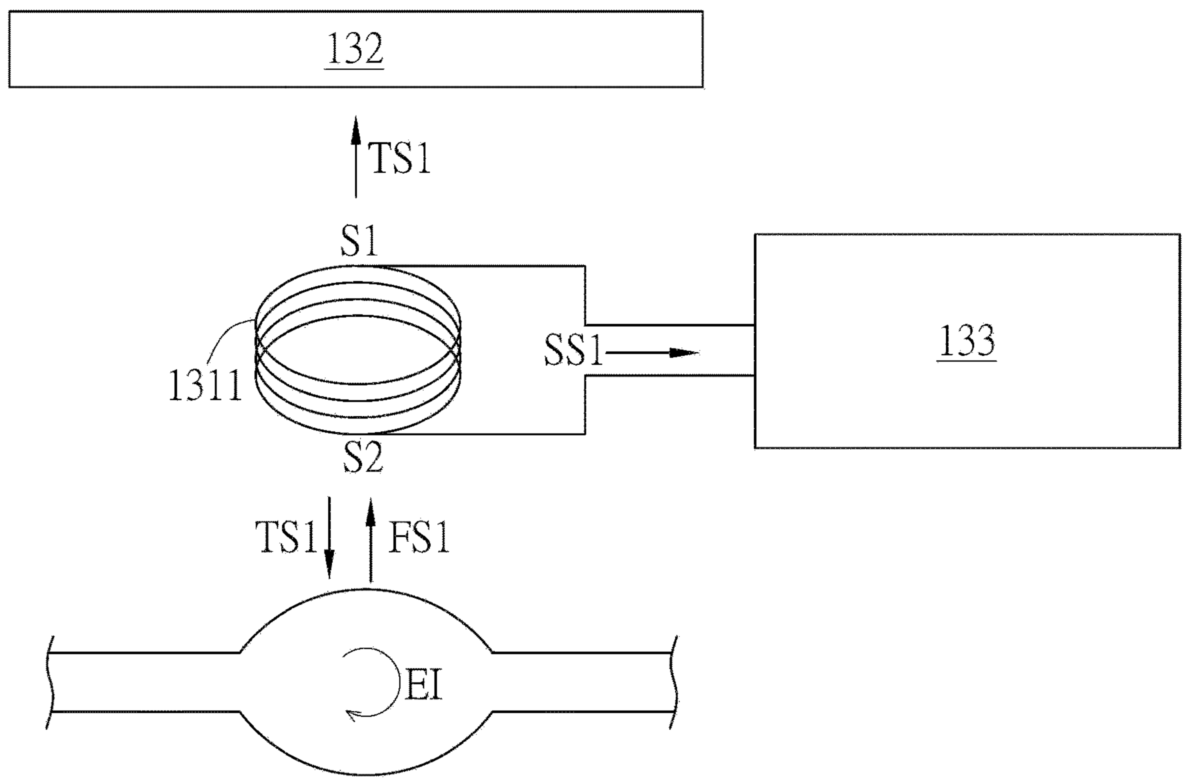

The control component 133 and the first coil 1311 are respectively configured to perform eddy current measurement on the user's wearing position. Specifically, as shown in FIG. 3, the control component 133 causes the first coil 1311 to generate a first emitting electromagnetic signal TS1 due to the electromagnetic effect. The first emitting electromagnetic signal TS1 will be emitted to the wearing part of the wearable device 10 (for example, the wrist). Because the tissue fluid or blood in the blood vessel in the wearing part has ions and is electrically conductive, the tissue fluid or blood in the blood vessel can be regarded as a planar conductor. When the tissue fluid or blood in the blood vessel receives the first emitting electromagnetic signal TS1, it will couple out an induced electric field and generate a corresponding eddy current EI. The magnitude of the eddy current EI can vary depending on the conductivity or the cross-sectional area or volume of the planar conductor. Eddy currents EI of different magnitudes generate a first feedback electromagnetic signal FS1 corresponding to the first emitting electromagnetic signal TS1 and in the opposite direction due to electromagnetic effects. By measuring the difference between the first emitting electromagnetic signal TS1 and the first feedback electromagnetic signal FS1, the current state of the tissue fluid or blood in the blood vessel can be calculated. It should be noted that the difference between the first emitted electromagnetic signal TS1 and the first feedback electromagnetic signal FS1 can be measured, for example, but not limited to, through the change in the inductance value of the first coil 1311 itself or by directly measuring the changes of the first feedback electromagnetic signal FS1 (for example, changes in frequency or amplitude).

In general, the current state of tissue fluid or blood in the blood vessel is closely related to the user's physiological information/status. Therefore, many studies have shown that the user's physiological information/status can be inferred based on the current state of tissue fluid or blood in blood vessels. In terms of blood vessel, because the blood in the blood vessel is driven by the contraction and relaxation of the heart, the amount of blood in the blood vessel will change with the heart rate/rhythm, which will lead to changes of the magnitude of the eddy current EI induced by the first emitting electromagnetic signal TS1 with respect to the heart rate/rhythm. Therefore, the user's heart rate/rhythm can be estimated from the current state of blood in the blood vessels. For example, when the blood vessel contracts, less blood participates in the conductor area that generates the eddy current, so the induced eddy current EI also has a smaller magnitude. However, the physiological information related to the blood and blood vessel of the user is not limited to the heart rate/rhythm. In the present invention, the blood vessel contraction and/or relaxation, pulse, blood vessel elasticity, intravascular status (for example, whether the inside of the blood vessel is clogged or unblocked, the status or the velocity of blood flow, etc.), blood vessel proliferation, blood vessel density, blood vessel wall status (for example, whether the blood vessel wall is damaged) and other medical/non-medical parameters should also be part of the physiological information/status related to the blood and blood vessel of the user. In another aspect, in the terms of tissue fluid, the conductivity of the tissue fluid is correlated with the user's physiological information (for example, blood glucose level). In other words, the user's physiological information (for example, high or low blood sugar level) will affect the conductivity of the tissue fluid. For example, under the measurement condition of 10 MHz frequency, the conductivity difference between the blood/tissue fluid of normal people and diabetic patients is about 40%. When the tissue fluid generates the eddy current EI in response to the first emitting electromagnetic signal TS1, the conductivity of the tissue fluid will affect the magnitude of the eddy current EI. Therefore, a corresponding model between conductivity and blood sugar can be established. For example, after measuring different blood glucose values through a prosthesis or phantom with tissue fluid or blood, the corresponding relationship of the difference between the first emitting electromagnetic signal TS1 and the first feedback electromagnetic signal FS1 and the physiological parameters can be obtained. This provides a calibration or correspondence table to establish a measurement correspondence model. However, the physiological information related to the tissue fluid of the user is not limited to the heart rate/rhythm. The "physiological information related to the tissue fluid" in the present invention includes, but is not limited to, blood sugar, inflammation status, osmotic pressure, or other physiological information related to the tissue fluid.

Through the correlation between the aforementioned sensing signal and the user's physiological status/information, the sensing module of the present invention can be configured to perform measurement or evaluation of the user's physiological status/information. However, the sensing module of the present invention is not limited to the human body. In other words, the sensing module of the present invention can be integrated into a wearable device and perform any application suitable for the eddy current sensing mechanism.

Figure 4A:
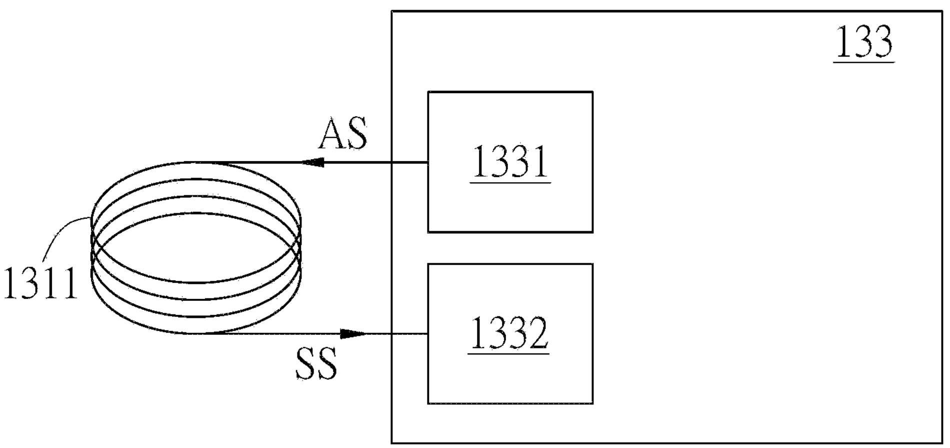
FIGS. 4A to 4D are schematic diagrams of the configuration of the control component in various embodiments of the present invention.

In an embodiment, please refer to FIG. 4A. The control component 133 includes an emitting unit 1331 and a receiving unit 1332 for generating the AC signal AS. The emitting unit 1331 may be an AC emitting unit 1331 composed of active components (e.g., oscillator, timer) and/or passive components (e.g., resistors, capacitors, inductors). For example, the emitting unit 1331 may directly generate the AC signal AS via the active/passive components. In another aspect, the emitting unit 1331 can convert the DC signal into the AC signal AS through a circuit consisting of active/passive components. For example, the emitting unit 1331 can oscillate the DC signal through the resonant circuit and then outputs the AC signal AS. Since the AC signal AS is generated by the resonant circuit, it can achieve benefits such as simplifying the circuit and saving energy consumption. In this embodiment, the frequency of the AC signal AS of the emitting unit 1331 is preferably 1-10 MHz. Therefore, the resonant frequency range of the resonant circuit is preferably 1-10 MHz or can output the AC signal AS mainly of 1-10 MHz.

Figure 4B:
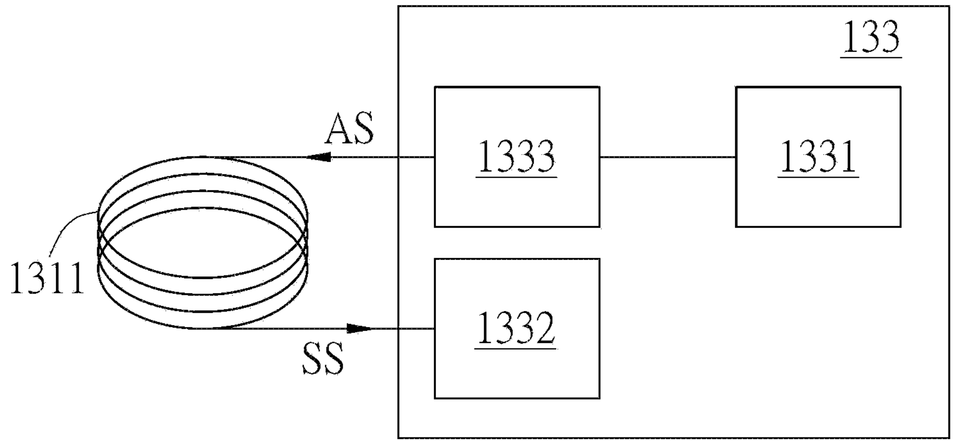
Figure 4C:
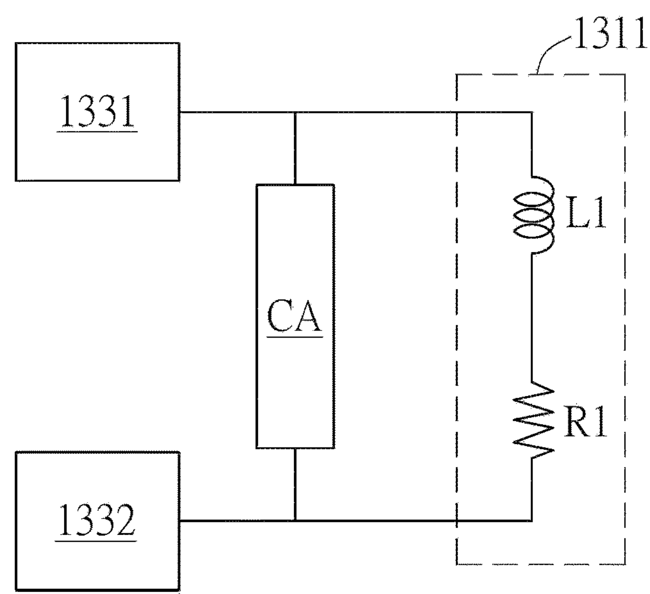

In this embodiment, please refer to FIG. 4B. The control component 133 may further include a frequency adjustment unit 1333 coupled between the first coil 1311 and the emitting unit 1331. The frequency adjustment unit 1333 is configured to adjust the frequency of the first emitting electromagnetic signal TS1. Specifically, the emitting unit 1331 generates the AC signal AS and outputs it to the first coil 1311, and the AC signal AS makes the first coil 1311 emit the first emitting electromagnetic signal. The first emitting electromagnetic signal is related to the frequency of the AC signal AS and the impedance value of the first coil 1311 itself. Therefore, the first emitting electromagnetic signal can be modified by adjusting the frequency of the AC signal AS or the impedance of the first coil 1311. For example, in FIG. 4C, the first coil 1311 can be equivalent to a series of an inductor Li and a resistor R1 in the circuit. In this embodiment, the frequency adjustment unit 1333 includes, for example, at least a capacitor array CA configured to adjust the impedance value of the first coil 1311. Through the series/parallel circuit arrangement of the capacitor array CA and the first coil 1311, an appropriate capacitor in the capacitor array CA can be selected to adjust the impedance value of the first coil 1311. By adjusting the frequency of the first emitting electromagnetic signal TS1, measurement can be performed at different depths or with different granularities, for example, so optimal user parameters can be used during the measurement process.

Figure 4D:
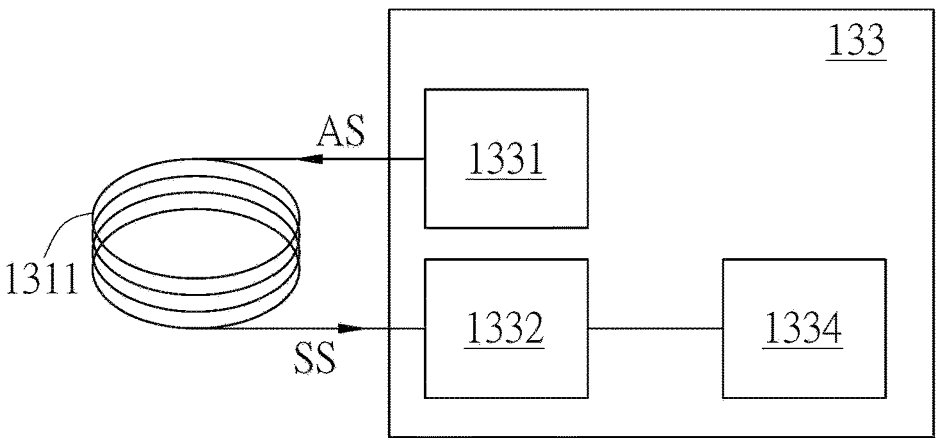

In another aspect, the receiving unit 1332 may, for example, sample or convert the induction signal SS from analog to digital and then perform calculation or measurement through a unit with computing capabilities. The receiving unit 1332 can perform signal analysis on the induction signal SS to obtain the frequency, amplitude, or other signal parameters of the induction signal SS. In this embodiment, please refer to FIG. 4D; the control component 133 may further include at least a computing unit 1334 coupled to the receiving unit 1332. Specifically, the computing unit 1334 can perform analysis based on the frequency, amplitude, or other signal parameters of the induction signal SS sampled by the receiving unit 1332, thereby calculating the physiological information of the wearer. It should be noted that the computing unit 1334 can be an individual or integrated chip, such as an application-specific integrated circuit (ASIC), a field programmable logic gate array (FPGA), a computing processor (CPU), a microprocessor, and other components with computing functions, which performs operations by fetching instruction sets or by other approaches. In another aspect, the computing unit 1334 can be the wearable device 10, a mobile phone, or a computer, which reads the instruction set stored in the memory to perform computing and analysis on the frequency, amplitude, or other signal parameters of the induction signal SS to obtain the user's physiological information. Through computing units 1334 with different computing capabilities, a balance can be found between cost and demand, avoiding problems such as wasting development costs and resources.

Figure 5A:
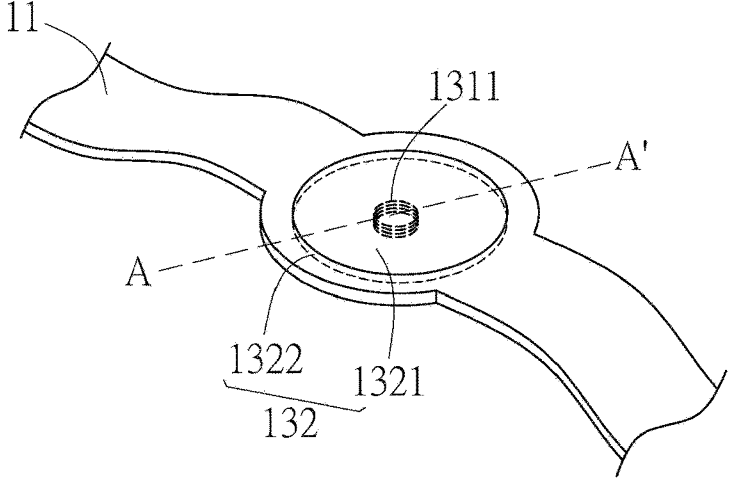
FIGS. 5A to 5E are schematic diagrams of the configuration of the shielding component in various embodiments of the present invention.
Figure 5B:
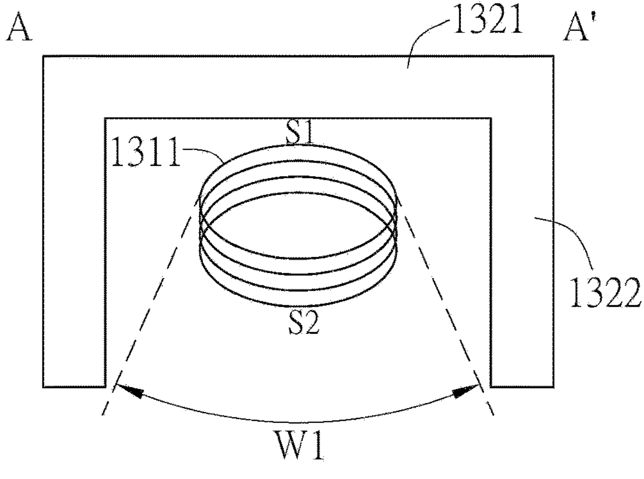
Figure 5C:
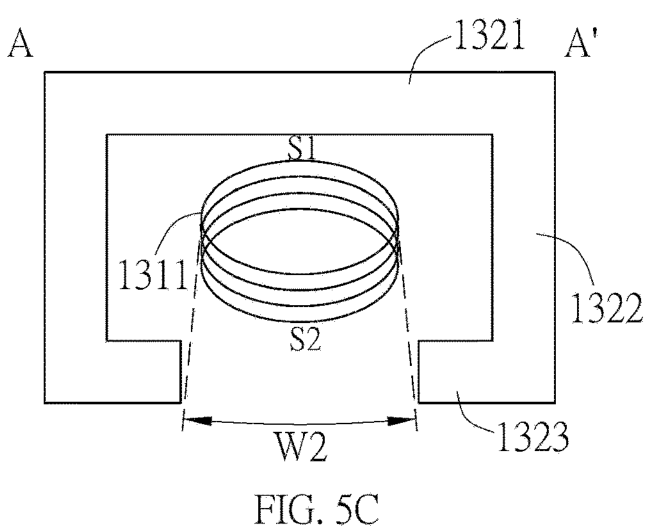
Figure 5D:
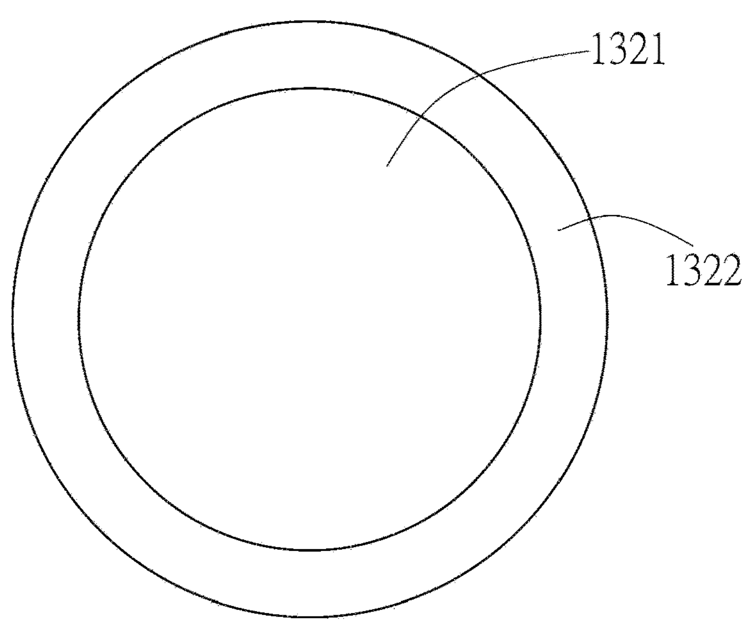
Figure 5E:
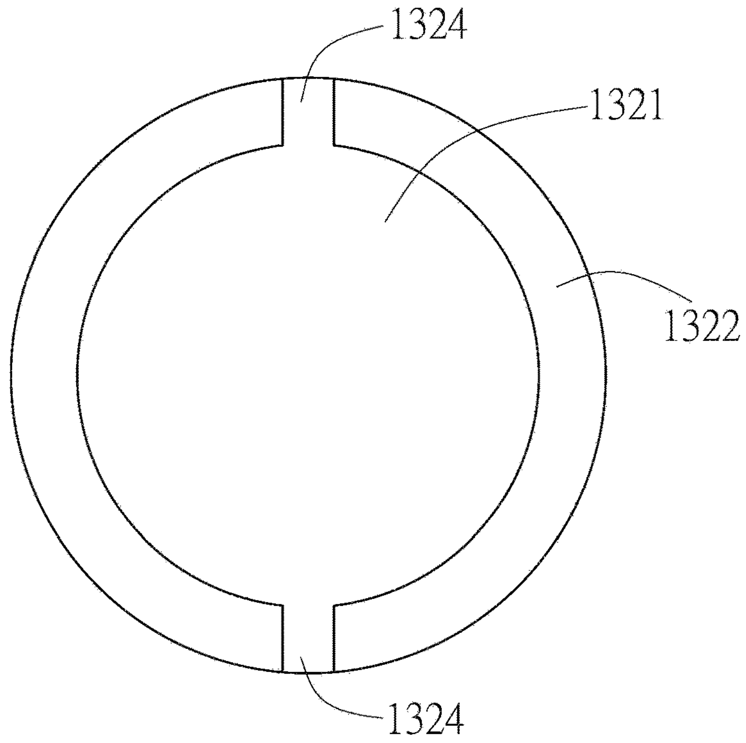

In an embodiment, please refer to FIGS. 5A to 5C, the shielding component 132 includes a shielding surface 1321 and a shielding wall 1322 surrounding the shielding surface 1321. The first coil 1311 is positioned inside the accommodating space formed by the shielding surface 1321 and the shielding wall 1322. Specifically, please refer to FIG. 5B, which shows a schematic cross-sectional view of the AA' area in FIG. 5A. The shielding surface 1321 can be positioned between the body 12 and the first coil 1311, thereby shielding the electromagnetic signal emitted from the first coil 1311 toward the body 12, and the shielding wall 1322 can be settled along the interior of the casing of the wearable device 10, for example. The shielding wall 1322 surrounds the first coil 1311 and has an opening W1, and the first emitting electromagnetic signal TS1 can be emitted outward through the opening W1. The portion of the first emitting electromagnetic signal TS1 that does not pass through the opening W1 will be shielded. By means of the shielding wall 1322, the emission range of the first emitting electromagnetic signal TS1 can be further limited, making the first emitting electromagnetic signal TS1 more directional. In this embodiment, please refer to FIG. 5C; the shielding wall 1322 has a contraction structure 1323 that partially shields the second side S2 of the first coil 131. For example, the contraction structure 1323 of the shielding wall 1322 can partially overlap the first coil 1311, thereby forming a smaller opening W2. The smaller opening can further limit the emission range of the first emitting electromagnetic signal TS1. By improving the directionality of the first emitting electromagnetic signal TS1, the energy of the first emitting electromagnetic signal TS1 can be concentrated and accurately transmitted to the target location. Furthermore, when receiving the feedback electromagnetic signal, it can receive the feedback electromagnetic signal induced and generated by the target location, which is not susceptible to noise interference. It should be noted that the contraction structure 1323 of the shielding wall 1322 may be fixed or movable. Taking the movable type as an example, the user can adjust the size and position of the opening according to the range and specific position of the target location, which can further improve the adjustability of measurement. It should be noted that, please refer to FIG. 5D and FIG. 5E, which are schematic views of the shielding component 132 from an upward perspective; the shielding wall 1322 does not have to be particularly complete. The shielding wall 1322 can further have at least one gap 1324 based on different requirements. The gap 1324 can be adjusted according to the shell interference of the wearable device 10. The gap 1324 can also improve the convenience of installation or serve as a fixing, positioning, or fool-proofing structure, but the use of gap 1324 is not limited to what being described here.

Figure 6A:
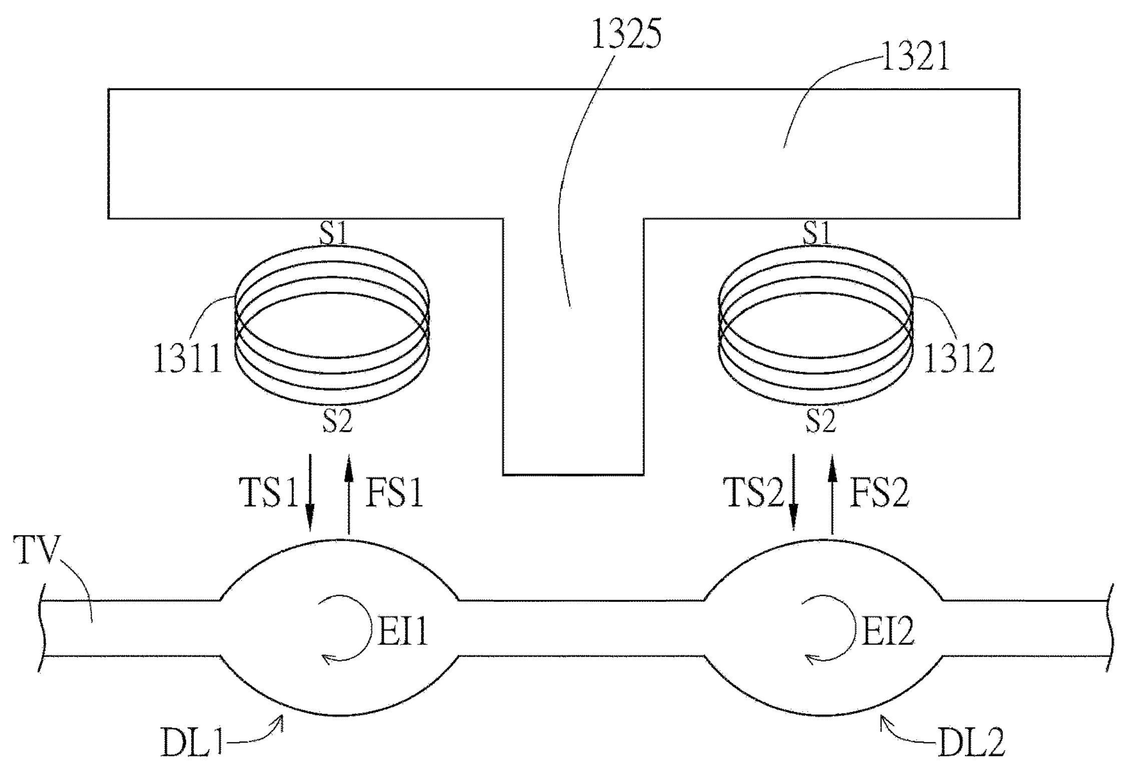
FIGS. 6A to 6C are schematic diagrams of a multi-coil configuration in an embodiment of the present invention.
Figure 6B:
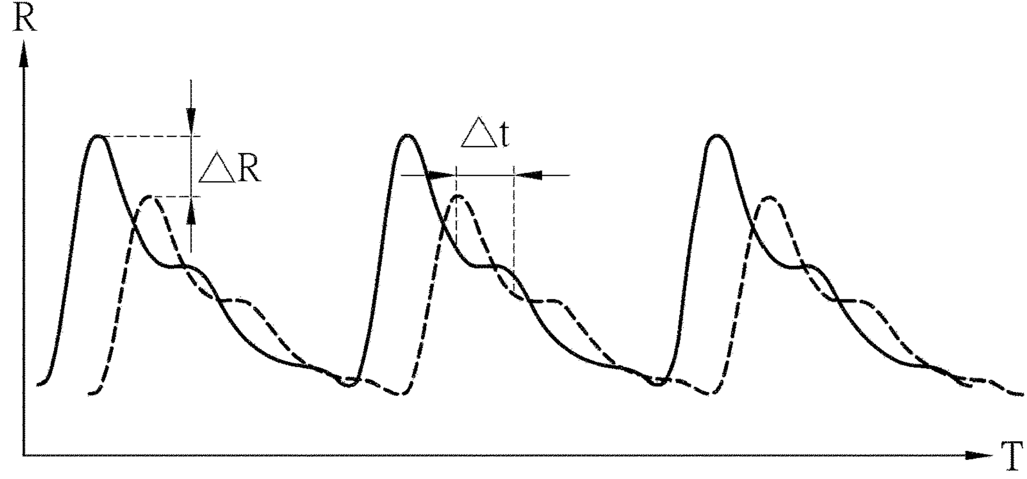

In an embodiment, as shown in FIGS. 6A and 6B, the sensing module 13 further includes a second coil 1312 adjacent to the first coil 1311. Eddy current measurement is performed on two sections of the blood vessel at the target location through the first coil 1311 and the second coil 1312, respectively. Specifically, after the first coil 1311 and the second coil 1312 transmit the first emitting electromagnetic signal TS1 and the second emitting electromagnetic signal TS2 respectively to the first measurement location DL1 and the second measurement location DL2 of the target blood vessel TV, it causes the first measurement location DL1 and the second measurement location DL2 of the target blood vessel TV to generate the corresponding eddy currents EI1 and EI2. It should be noted that the magnitude, frequency, and/or time difference of the eddy currents EI1 and EI2 will vary according to the blood vessel conditions at the first measurement location DL1 and the second measurement location DL2. For example, when fat or foreign matter causes embolism between the first measurement location DL1 and the second measurement location DL2, the blood flow pressures at the first measurement location DL1 and the second measurement location DL2 will be different. As a result, the degree of contraction/relaxation of the target blood vessel TV at the first measurement location DL1 and the second measurement location DL2 is different, thereby affecting the magnitude of the generated eddy currents EI1 and EI2. In another example, the pulse wave velocity (PWV) in the target blood vessel TV will also affect the time difference between the generation of eddy currents EI1 and EI2. Specifically, the contraction/relaxation time difference between the target blood vessel TV at the first measurement location DL1 and the second measurement location DL2 due to pulse propagation will cause a time difference between the generation of eddy currents EI1 and EI2. The eddy currents EI1 and EI2 induced by the target blood vessel TV at the first measurement location DL1 and the second measurement location DL2 will generate the first feedback electromagnetic signal FS1 and the second feedback electromagnetic signal FS2, respectively. The difference in signal characteristics (for example, frequency, peak time difference) between the first feedback electromagnetic signal FS1 and the second feedback electromagnetic signal FS2 will be different due to the difference in eddy currents EI1 and EI2. The first feedback electromagnetic signal FS1 and the second feedback electromagnetic signal FS2 are received respectively and converted into induction signals, for example, through analog conversion or digital conversion to facilitate subsequent signal processing.

The computing unit 1334 computes at least one blood vessel status of the target blood vessel TV according to the difference of signal characteristic between the first feedback electromagnetic signal FS1 and the second feedback electromagnetic signal FS2. The vascular status is, for example, vascular embolism (between the first measurement location DL1 and the second measurement location DL2), vascular sclerosis, pulse transmission speed, estimated blood flow velocity, etc. For example, as shown in FIG. 6B, X-axis is time or a time-dependent data component (for example, the Nth data), and the Y-axis is the response R, which is the measurable numeric calculated from the first feedback electromagnetic signal FS1 and the second feedback electromagnetic signal FS2, where the measurable numeric can be the amplitude, frequency, changes of frequency, inductance, changes of inductance, or other signal parameters. By measuring the response difference ΔR between the first feedback electromagnetic signal FS1 and the second feedback electromagnetic signal FS2 corresponding to the eddy currents EI1 and EI2, the vascular embolism situation can be assessed based on the response difference ΔR. Specifically, experimental approaches such as big data or simulation experiments can be used to find the relationship curve between the response difference ΔR and the degree of vascular embolism. By building a table or other data comparison methods, when the response difference ΔR is measured, the extent of embolism of the blood vessel can be estimated. In another aspect, the pulse propagation rate (PWV) can be calculated through the distance D between the first measurement location DL1 and the second measurement location DL2 as well as the peak time difference Δt between the first feedback electromagnetic signal FS1 and the second feedback electromagnetic signal FS2. Specifically, the pulse transmits through the contraction and relaxation of the blood vessel driven by the blood pumped from the heart. The higher the degree of vascular sclerosis is, the higher the pulse propagation rate (PWV) will be. Therefore, the degree of vascular sclerosis of the target blood vessel TV can be evaluated through the pulse propagation velocity (PWV). It should be noted that the above application examples are only used to illustrate how the present invention calculates the status of blood vessel, and are not intended to limit the present invention. In addition, conventional techniques can complement with corrections for such as heartbeat, blood pressure, age of the user, or other parameters to make the assessment of the vascular status more accurate. Moreover, in the present invention, long-term measurement of the user can also be used to compare various parameters of the target blood vessel TV in the past and the current time to evaluate the vascular status of the target blood vessel TV.

In this embodiment, the shielding component 132 may include an isolation wall 1325 positioned between the first coil 1311 and the second coil 1312, thereby separating the first coil 1311 and the second coil 1312. Due to its electrical characteristics, the isolation wall 1325 can reduce mutual interference between the first coil 1311 and the second coil 1312. In another aspect, in terms of mechanical structural characteristics, the isolation wall 1325 can serve as an auxiliary structure to increase the overall structural strength.

Figure 6C:
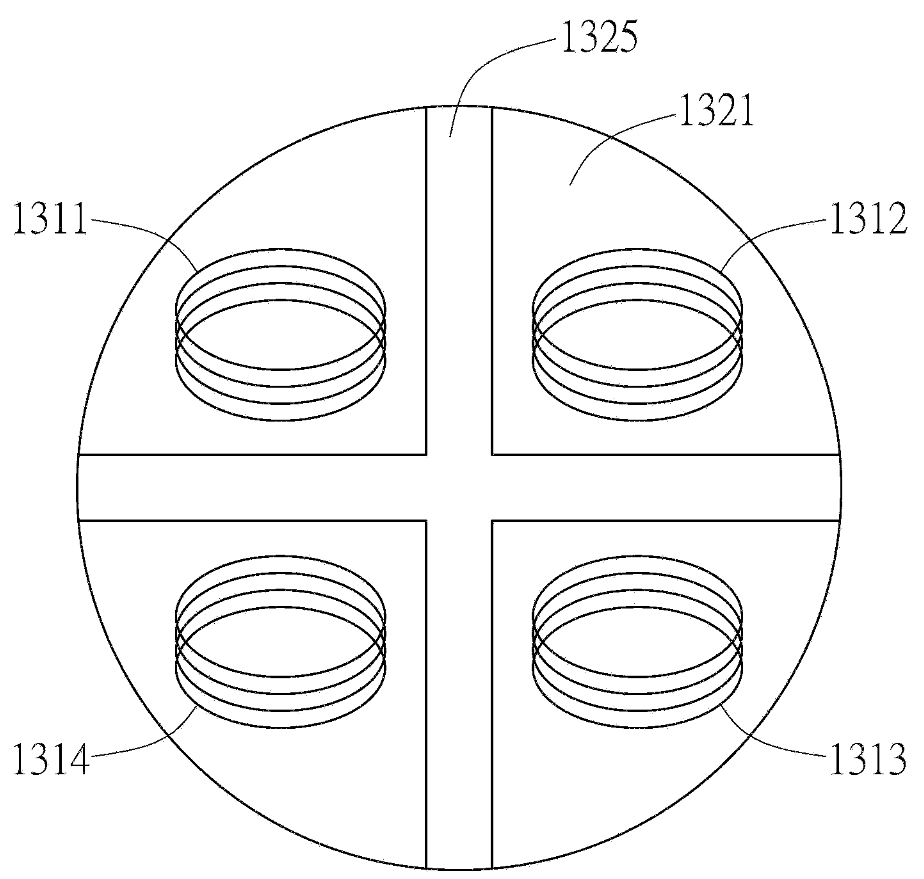

It should be noted that in this embodiment, only two coils are used for illustration to simplify the description. However, the present invention is not limited to the number of coils. Specifically, please refer to FIG. 6C, the number of coils may be more than two. By arranging multiple coils 1311-1314, the measurement range of the sensing module 13 can be extended from a one-dimensional direction to a two-dimensional direction. By comparing the induction signals SS of multiple coils with each other, a more accurate blood flow direction or blood vessel distribution range can be obtained, thereby improving the measurement accuracy. In this embodiment, isolation walls 1325 can also be provided between multiple coils for isolation to reduce mutual influence between each other.

In an embodiment, the sensing module 13 may further include a matching component positioned on the second side S2 of the first coil 1311. Specifically, the matching component may be, for example, but not limited to, positioned on the casing of the wearable device or the shielding wall 1322 in the aforementioned embodiment. The criteria for selecting the matching component can be based on its magnetic impedance. For example, a material whose magnetic impedance is between air and skin is selected as the matching component. The matching component can effectively improve electromagnetic wave transmission efficiency and reduce transmission losses caused by impedance mismatch such as attenuation or reflection. In this way, the energy required by the first coil 1311 to complete the measurement can be reduced, and the impact or interference on the surroundings (for example, the body 12 of the wearable device 10) can be reduced. It should be noted that the matching component of the present invention focuses on parameters such as magnetic impedance, so there is no restriction on the appearance or transmittance of the material. The matching component will not affect the appearance design of the wearable device 10 and can be integrated into the appearance design of the wearable device 10. It should be noted that the present invention is not limited to the existence of the matching component; even if no matching component is incorporated, the sensing mechanism of the present invention can also significantly relax the requirements for transmittance or scratch resistance of the casing in traditional optical measurement. The impact on the body of the wearable device 10 is reduced.

In summary, the sensing module 13 of the present invention can perform eddy current induction measurement on the wearing position through one or more coils. Because eddy current induction measurement is a non-contact measurement mechanism based on electromagnetic signals, the penetration depth or range can be adjusted by adjusting the transmission frequency or the number of other coils. It is not easily affected by skin or other non-conductive media in the transmission pathway, so it has good interference resistance. Furthermore, the shielding component 132 is used to limit the range of the electromagnetic signal emitted by the coil. This makes the electromagnetic signal emitted by the coil more directional and reduces the impact of the sensing module 13 on surrounding circuit components or other sensing modules 13. Moreover, due to the measurement mechanism of electromagnetic signals, the casing of the wearable device 10 (the side that contacts the user) is not limited to being transparent and capable of guiding light, so it has little impact on the appearance design of the wearable device 10, and it relaxes the waterproof and dustproof requirement or their difficulties to be configured.

The provided description of the invention enables a person of ordinary skill in the art to make or practice the invention. Various modifications to the invention will be apparent to those skilled in the art, and the general principles defined herein may be applied to other changes without departing from the spirit or scope of the invention. Thus, the present invention is not intended to be limited to the examples described herein but is to be accorded the widest scope consistent with the principles and novel features of the invention herein.

What is claimed is:

1. A sensing module for a wearable device, including:
- a first coil having a first side toward to the wearable device, and a second side opposite to the first side;
- a control circuitry coupled to the first coil, wherein the control circuitry is configured to drive the first coil to transmit a first emitting electromagnetic signal to a wearing portion of the wearable device, and to receive a first induction signal generated from the first coil in response to a first feedback electromagnetic signal; and
- a shielding component forming an accommodating space for the first coil, the shielding component including:
- a shielding surface positioned at the first side,
- a shielding wall surrounding the first coil, and
- a contraction structure extending from the shielding wall toward an axis of the first coil to define a restricted opening at the second side of the first coil.

2. The sensing module of claim 1, wherein the contraction structure at least partially overlaps the second side of the first coil to concentrate the first emitting electromagnetic signal through the restricted opening.

3. The sensing module of claim 1, further including a second coil disposed adjacent to the first coil.

4. The sensing module of claim 3, wherein the shielding component includes an isolation wall positioned between the first coil and the second coil.

5. The sensing module of claim 1, further including a matching component positioned at a second side of the first coil.

6. The sensing module of claim 1, wherein the control circuit includes an emitting unit and a receiving unit, wherein the emitting unit is configured to drive the first coil to transmit the first emitting electromagnetic signal, and the receiving unit is configured to receive the first induction signal generated from the first coil due to the first feedback electromagnetic signal.

7. The sensing module of claim 6, wherein the control circuit further includes a frequency adjustment unit coupled between the first coil and the emitting unit, wherein the frequency adjustment unit is configured to adjust a frequency of the first emitting electromagnetic signal.

8. The sensing module of claim 7, wherein the frequency adjustment unit includes at least a capacitor array configured to adjust an impedance value of the first coil.

9. The sensing module of claim 6, wherein the control circuit further includes a computing unit connected at least to the receiving unit, wherein the computing unit is configured to calculate physiological information based on the first induction signal.

10. A wearable device, including:
- a wearing structure;
- a body combined with the wearable structure; and
- a sensing module, including:
- a first coil having a first side toward to the wearable device, and a second side opposite to the first side;
- a control circuitry coupled to the first coil, wherein the control circuitry is configured to drive the first coil to transmit a first emitting electromagnetic signal to a wearing portion of the wearable device, and to receive a first induction signal generated from the first coil in response to a first feedback electromagnetic signal; and
- a shielding component forming an accommodating space for the first coil, the shielding component including:
- a shielding surface positioned at the first side,
- a shielding wall surrounding the first coil, and
- a contraction structure extending from the shielding wall toward an axis of the first coil to define a restricted opening at the second side of the first coil;
- wherein the body is positioned on the first side of the sensing module, and the shielding component of the sensing module is positioned at least between the body and the first coil of the sensing module.

11. The wearable device of claim 10, wherein the contraction structure at least partially overlaps the second side of the first coil to concentrate the first emitting electromagnetic signal through the restricted opening.

12. The wearable device of claim 10, wherein the sensing module further includes a second coil disposed adjacent to the first coil.

13. The wearable device of claim 12, wherein the shielding component includes an isolation wall positioned between the first coil and the second coil.

14. The wearable device of claim 10, wherein the sensing module further includes a matching component positioned at a second side of the first coil.

15. The wearable device of claim 10, wherein the control circuit includes an emitting unit and a receiving unit, wherein the emitting unit is configured to drive the first coil to transmit the first emitting electromagnetic signal, and the receiving unit is configured to receive the first induction signal generated from the first coil due to the first feedback electromagnetic signal.

16. The wearable device of claim 15, wherein the control circuit further includes a frequency adjustment unit coupled between the first coil and the emitting unit, wherein the frequency adjustment unit is configured to adjust a frequency of the first emitting electromagnetic signal.

17. The wearable device of claim 16, wherein the frequency adjustment unit includes at least a capacitor array configured to adjust an impedance value of the first coil.

18. The wearable device of claim 15, wherein the control circuit further includes a computing unit connected at least to the receiving unit, wherein the computing unit is configured to calculate physiological information based on the first induction signal.

* * * * *